United States Patent
Neumann et al.

(10) Patent No.: US 12,236,604 B2
(45) Date of Patent: Feb. 25, 2025

(54) METHOD FOR PROVIDING AIRWAY INFORMATION

(71) Applicant: Siemens Healthcare GmbH, Erlangen (DE)

(72) Inventors: Dominik Neumann, Erlangen (DE); Puyang Wang, Baltimore, MD (US); Anna Boehm, Stuttgart (DE); Sasa Grbic, Plainsboro, NJ (US); Zhoubing Xu, Plainsboro, NJ (US); Siqi Liu, Princeton, NJ (US)

(73) Assignee: SIEMENS HEALTHINEERS AG, Forchheim (DE)

(*) Notice: Subject to any disclaimer, the term of this patent is extended or adjusted under 35 U.S.C. 154(b) by 481 days.

(21) Appl. No.: 17/177,286

(22) Filed: Feb. 17, 2021

(65) Prior Publication Data
US 2021/0272287 A1    Sep. 2, 2021

(30) Foreign Application Priority Data

Feb. 28, 2020  (EP) .................................. 20160072

(51) Int. Cl.
*G06T 7/00*    (2017.01)
*G06T 7/11*    (2017.01)
(Continued)

(52) U.S. Cl.
CPC ............... *G06T 7/11* (2017.01); *G16H 30/00* (2018.01); *G16H 50/20* (2018.01);
(Continued)

(58) Field of Classification Search
CPC ............. G06T 7/11; G06T 2207/20076; G06T 2207/20081; G06T 2207/20084;
(Continued)

(56) References Cited

U.S. PATENT DOCUMENTS

| 10,258,304 | B1 | 4/2019 | Kiraly et al. |
| 2007/0049840 | A1* | 3/2007 | Odry ..................... G16H 30/40 600/532 |

(Continued)

FOREIGN PATENT DOCUMENTS

| CN | 110378923 A | 10/2019 |
| DE | 10326817 A1 | 12/2004 |

(Continued)

OTHER PUBLICATIONS

Yun et al. Improvement of fully automated airway segmentation on volumetric computed tomographic images using a 2.5 dimensional convolutional neural net☆ (Year: 2019).*

(Continued)

*Primary Examiner* — Vu Le
*Assistant Examiner* — Winta Gebreslassie
(74) *Attorney, Agent, or Firm* — Harness, Dickey & Pierce, P.L.C.

(57) ABSTRACT

A computer-implemented method is for providing quantitative airway information. In an embodiment, the method includes receiving and/or determining first medical image data of an airway segment; applying a first trained function to the first medical image data, to generate output data; determining the at least one quantitative airway information of the airway segment based on the output data; and providing the at least one quantitative airway information.

20 Claims, 7 Drawing Sheets

(51) Int. Cl.
*G16H 30/00* (2018.01)
*G16H 50/20* (2018.01)

(52) U.S. Cl.
CPC ............... *G06T 2207/20076* (2013.01); *G06T 2207/20081* (2013.01); *G06T 2207/20084* (2013.01); *G06T 2207/30061* (2013.01)

(58) Field of Classification Search
CPC . G06T 2207/30061; G06T 2207/10081; G06T 2207/20168; G06T 7/0012; G06T 7/12; G06T 7/136; G06T 7/155; G16H 30/00; G16H 50/20; A61B 6/5217; A61B 6/032; A61B 6/037; A61B 8/5223; G06N 3/045; G06N 3/047; G06N 3/084
See application file for complete search history.

(56) References Cited

U.S. PATENT DOCUMENTS

| | | | |
|---|---|---|---|
| 2015/0141814 A1 | 5/2015 | Lee et al. | |
| 2018/0068446 A1* | 3/2018 | Ross | G06T 7/0016 |
| 2019/0059840 A1 | 2/2019 | Fouras et al. | |
| 2019/0139227 A1* | 5/2019 | Wang | G06F 18/24 |
| 2019/0220701 A1* | 7/2019 | Novak | G06F 18/2113 |
| 2021/0201495 A1* | 7/2021 | Yu | A61B 5/7264 |

FOREIGN PATENT DOCUMENTS

| | | |
|---|---|---|
| DE | 102008061170 A1 | 7/2009 |
| EP | 2875781 A1 | 5/2015 |

OTHER PUBLICATIONS

Jean-Paul "Improving airway segmentation in computed tomography using leak detection with convolutional networks" (Year: 2017).*

Feuerstein, M. et. al., "Adaptive Branch Tracing and Image Sharpening for Airway Tree Extraction in 3-D Chest CT," Proceedings of 2nd International Workshop on Pulmonary Image Analysis, p. 273-284, 2009.

pytorch.org, loss functions, https://pytorch.org/docs/stable/nn.html#loss-functions, Stand: Mar. 20, 2020.

Cicek, Özgün et al.: "3D U-Net: Learning Dense Volumetric Segmentation from Sparse Annotation"; 2016; arXiv:1606.06650; 2016.

Charbonnier Jean-Paul et al; "Improving airway segmentation in computed tomography using leak detection with convolutional networks"; Medical image analysis; vol. 36; Nov. 4, 2016; pp. 52-60; XP029882420; ISSN: 1316-8415; DOI: 10.1016/J.Media.2016.11.001.

Jun Tan et al; "Two-dimensional airway analysis using probabilistic neural networks"; SPIE—International society for optical engineering. proceedings: vol. 7626; Mar. 4, 2010 (Mar. 4, 2010); p. 762612; XP055703532; US; ISSN: 0277-786X; DOI: 10.1117/12.844497.

Coxson, H.O., "Quantitative computed tomography assessment of airway wall dimensions: current status and potential applications for phenotyping chronic obstructive pulmonary disease", in: Proceedings of the American Thoracic Society, 5(9), pp. 940-945,2008.; 2008.

Irving, B. et. al., "3D segmentation of the airway tree using a morphology based method", Proceedings of 2nd International Workshop on Pulmonary Image Analysis, p. 297-307, 2009.

Schlemper, J. et. al., "Attention-Gated Networks for Improving Ultrasound Scan Plane Detection", 1st Conference on Medical Imaging with Deep Learning (MIDL) 2018, arXiv: 1804:05338v1, 2018.

Siqi, L. et. al., "Automated 3-D Neuron Tracing With Precise Branch Erasing and Confidence Controlled Back Tracking", IEEE Transactions on Medical Imaging, vol. 37, No. 11: 2441-2452, 2018.

Sang Joon Park et al; "A Color-coded Virtual Bronchoscopy with Enhanced Efficiency"; Biomedical engineering and informatics; 2008; BMEI 2008; International conference on; IEEE; Piscataway; NJ; USA; May 27, 2008; pp. 770-774; XP031275787; ISBN: 978-0-7695-31118-2.

Nakano, Y. et. al., "The prediction of small airway dimensions using computed tomography", Am. J. Resp. Crit. Care, 171(2), pp. 142-146, 2005.

Bauer, C. et. al., "Airway Tree Reconstruction Based on Tube Detection", Proceedings of 2nd International Workshop on Pulmonary Image Analysis, p. 203-213 2009.

Lo, P. et. al., "Multiscale Vessel-guided Airway Tree Segmentation", Proceedings of 2nd International Workshop on Pulmonary Image Analysis, p. 323-332, 2009.

Pu Jiantao et al: "CT based computerized identification and analysis of human airways: A review"; Medical physics; AIP; Melville; NY; US; vol. 39; No. 5; May 1, 2012; pp. 2603-2616; XP012161017; ISSN: 0094-2405; DOI: 10.1118/1.4703901.

Reinhardt, J. M. et. al., "Accurate measurement of intrathoracic airways", IEEE Trans. Med. Imaging, 16(6), pp. 820-827, 1997.

Extended European Search Report dated Jun. 24, 2020.

* cited by examiner

METHOD FOR PROVIDING AIRWAY INFORMATION

PRIORITY STATEMENT

The present application hereby claims priority under 35 U.S.C. § 119 to European patent application number EP20160072.3 filed Feb. 28, 2020, the entire contents of which are hereby incorporated herein by reference.

FIELD

Example embodiments of the application generally relates to a method and a device for automatic determination of airway information based on medical images.

BACKGROUND

Chronic obstructive pulmonary disease (acronym "COPD") is the third leading cause of death worldwide and claimed 3 million lives in 2016. Clinical studies have shown correlations between wall thickening in small airways and airflow limitation indicating COPD. It is therefore of high clinical interest to detect and quantify abnormal airway walls. Wall thickening can be assessed by imaging, in particular high-resolution computed tomography (acronym "CT") of the lung/thorax.

Lung CT images can be analyzed manually by radiologists or other experienced medical experts by manually browsing through CT slices and searching for visual indications of abnormal wall thickness or other signs of inflammation. This is however quite tedious, time-consuming and can be error-prone due to the large number of airway segments, in particular for the small airways, which are most relevant for COPD assessment.

Some work has been described on semi-automatic or automatic estimation of airway dimension for large- to intermediate-size airways (Nakano, Y. et al., The prediction of small airway dimensions using computed tomography, Am. J. Resp. Crit. Care, 171(2), pp. 142-146, 2005). However, due to very limited number of datasets, these methods are often not validated and tested properly on unseen data. The majority of methods are designed to analyze airway walls on extracted two-dimensional patches of three-dimensional CT images.

To this end, an airway centerline tree is needed as input in order to define precisely the location and orientation for the two-dimensional patch extraction to achieve optimal quantification results. Ideally, airways should be centered in the 2D patches and appear circular. With other words the airway direction should be orthogonal to the two-dimensional plane. Then, oftentimes "full width half maximum" (acronym "FWHM") or related methods are applied to analyze intensity profiles to delineate inner and outer airway walls. As described by Reinhardt et al., "Accurate measurement of intrathoracic airways" (IEEE Trans. Med. Imaging, 16(6), pp. 820-827, 1997) for instance, applying standard FWHM on such 2D patches can provide good results for airways with large diameters and thick walls, but is biased for small airways and thin walls.

The extraction of airway trees in chest volumetric CT scans are defined as extracting lung airway tree structure and its image coordinates as accurate and complete as possible. It plays an important role in the analysis of lung airway diseases. One application of airway tree extraction is in the measurement of airway lumen and wall dimensions, which have been shown to correlate well with the presence of COPD.

As the lungs are subdivided anatomically based on the airway tree, airway tree extraction is also a useful input for other segmentation tasks such as segmentation of lobes. In addition, airway tree extraction also plays an important role in navigated bronchoscopy systems where airway centerline-based registration of preoperative images to a patient's anatomy is commonly used.

Airway centerline extraction can be very challenging due to the thin and unclear tubular structure of smaller airway branches. Due to this structural complexity, the extraction is tedious and time consuming using manual or semi-automatic methods, taking more than 7 h or up to 2.5 h, respectively. In addition, annotations may be error prone and inconsistent. Many automatic methods have been reported, including threshold-based, morphology-based and 2D learning-based. However, the extracted airway branches are often limited in depth and continuity due to the failure of exploiting 3D spatial information and gap connecting capability.

Hence, the full automated extraction of the airway tree is beneficial for providing a full automated COPD assessment.

SUMMARY

At least one embodiment of the present invention provides a full-automatic COPD assessment based on medical images.

Embodiments of the present invention are directed to a method, a providing system, a computer program product and a computer-readable storage medium. Advantageous further developments are listed in the claims and in the following specification.

In a first embodiment, the invention relates to a computer-implemented method for providing at least one quantitative airway information. The computer-implemented method comprises receiving and/or determining first medical image data of an airway segment. In a further step, the method comprises applying a first trained function to the first medical image data, wherein output data is generated. In a further step, the method comprises determining the at least one quantitative airway information of the airway segment based on the output data. In a further step, the method comprises providing the at least one quantitative airway information.

In a second embodiment, the invention relates to a computer implemented method for providing a first trained function. The method comprises receiving first medical image data of a first airway segment, receiving first annotated data, wherein the first annotated data is based on the first medical image data, wherein the first annotated data is a mask of a wall of the airway segment, training the first trained function based on the first medical image data and the first annotated data, and providing the first trained function.

In a third embodiment, the invention relates to a first providing system for providing quantitative airway information. The first providing system comprises an interface and a computation unit, wherein the interface and/or the computation unit are configured for receiving and/or determining first medical image data of an airway segment, wherein the computation unit is furthermore configured for applying a first trained function to the first medical image data, wherein output data is generated, wherein the computation unit is furthermore configured for determining the at least one quantitative airway information of the airway segment based on the output data, wherein the interface is furthermore configured for providing the at least one quantitative airway information.

In a fourth embodiment, the invention relates to a computer program product with a computer program and a computer-readable medium. A mainly software-based implementation has the advantage that even previously used first providing systems can be easily upgraded by a software update in order to work in the manner described. In addition to the computer program, such a computer program product can optionally include additional components such as documentation and/or additional components, as well as hardware components such as e.g. hardware keys (dongles etc.) for using the software.

In a further embodiment, the invention relates to a computer program product comprising program elements directly loadable into a memory unit of a first providing system, which induces the first providing system to execute the method according to the claimed method and its embodiments when the program elements are executed by the first providing system.

In a fifth embodiment, the invention relates to a computer-readable storage medium comprising program elements which are readable and executable by a first providing system, to execute the claimed method and its embodiments, when the program elements are executed by the first providing system.

In a further embodiment, the invention relates to a computer-readable storage medium, comprising a first trained function as of at least one embodiment.

In an embodiment, the invention relates to a computer-implemented method for providing at least one quantitative airway information, comprising:
  at least one of receiving and determining first medical image data of an airway segment;
  applying a first trained function to the first medical image data, to generate output data;
  determining the at least one quantitative airway information of the airway segment based on the output data; and
  providing the at least one quantitative airway information.

In an embodiment, the invention relates to a computer implemented method for providing a first trained function, comprising:
  receiving first medical image data of a first airway segment;
  receiving first annotated data, the first annotated data being based on the first medical image data, and the first annotated data being a mask of a wall of the first airway segment;
  training the first trained function based on the first medical image data and the first annotated data; and
  providing the first trained function.

In an embodiment, the invention relates to a first providing system for providing at least one quantitative airway information, comprising:
  an interface; and
  a computation unit,
  at least one of the interface and the computation unit being configured to at least one of receive and determine first medical image data of an airway segment,
  the computation unit being configured to apply a first trained function to the first medical image data, to generate output data,
  the computation unit being configured to determine the at least one quantitative airway information of the airway segment based on the output data, and
  the interface being configured to provide the at least one quantitative airway information.

In an embodiment, the invention relates to a non-transitory computer program product storing program elements, directly loadable into a memory unit of a first providing system, to induce a providing system to execute the method of an embodiment when the program elements are executed by the providing system.

In an embodiment, the invention relates to a non-transitory computer-readable storage medium storing program elements, readable and executable by a providing system, to execute the method of an embodiment when the program elements are executed by the providing system.

In an embodiment, the invention relates to a non-transitory computer-readable storage medium, storing the first trained function provided by the method of an embodiment.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

DETAILED DESCRIPTION OF THE EXAMPLE EMBODIMENTS

Figure 1:
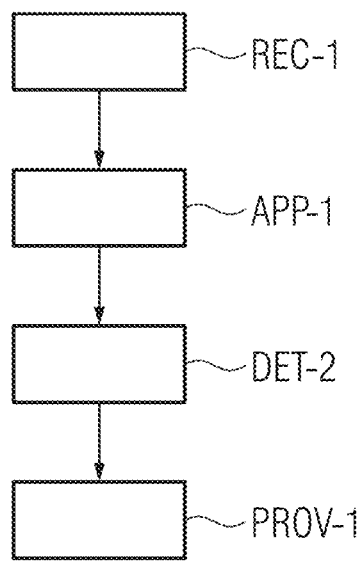
FIG. 1 displays a schematic flow chart of a first embodiment of the method for providing a quantitative airway information, FIG. 2 displays a schematic flow chart of a second embodiment of the method for providing a quantitative airway information, FIG. 3 displays a schematic flow chart of a third embodiment of the method for providing a quantitative airway information, FIG. 4 displays a schematic flow chart of a fourth embodiment of the method for providing a quantitative airway information, FIG. 5 displays a schematic flow chart of the data according to the fourth embodiment according to FIG. 4, FIG. 6 displays an illustrated flow chart of the data according to FIG. 5, FIG. 7 displays a schematic flow chart of an embodiment of a method for providing a first trained function, FIG. 8 displays a providing system, FIG. 9 displays a training system.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Bluray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Bluray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable nonvolatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable nonvolatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In the following, embodiments according to the invention are described with respect to the systems as well as with respect to the methods. Features, advantages or alternative embodiments herein can be assigned to the other objects and vice versa. In other words, claims and embodiments for the providing systems can be improved with features described or claimed in the context of the methods. In this case, the functional features of the method are embodied by objective units of the providing system.

Furthermore, in the following, embodiments according to the invention are described with respect to methods and systems for providing at least one quantitative airway information as well as with respect to methods and systems for providing a trained function. Features, advantages or alternative embodiments herein can be assigned to the other claimed objects and vice versa. In other words, claims and embodiments for methods and systems for providing the trained function can be improved with features described or claimed in context of the methods and systems for providing the at least one quantitative airway information, and vice versa.

In particular, the trained function used within the methods and systems for providing the at least one quantitative airway information can be adapted by the methods and systems for providing the trained function. Furthermore, input data used in the methods and systems for providing the at least one quantitative airway information can comprise advantageous features and embodiments of training input data used in the methods and systems for providing the trained function, and vice versa. Furthermore, output data used in the methods and systems for providing the at least one quantitative airway information can comprise advantageous features and embodiments of output training data used in the methods and systems for providing the trained function, and vice versa.

In a first embodiment, the invention relates to a computer-implemented method for providing at least one quantitative airway information. The computer-implemented method comprises receiving and/or determining first medical image data of an airway segment. In a further step, the method comprises applying a first trained function to the first medical image data, wherein output data is generated. In a further step, the method comprises determining the at least one quantitative airway information of the airway segment based on the output data. In a further step, the method comprises providing the at least one quantitative airway information.

In particular, the step of receiving and/or determining first medical image data is executed by an interface and/or a computation unit, in particular, by an interface and/or a computation unit of the providing system. In particular, the step of applying the first trained function is executed by the computation unit, in particular, by the computation unit of the providing system. In particular, the step of determining the at least one quantitative airway information is executed by the computation unit, in particular, by the computation unit of the providing system. In particular, the step of providing the at least one quantitative airway function is executed by the interface unit, in particular by the interface unit of the providing system.

In particular, the step of applying the first trained function is executed after the step of receiving and/or determining first medical image data. In particular, the step of determining the at least one quantitative airway information is executed after the step of applying the first trained function. In particular, the step of providing the at least one quantitative airway information is executed after the step of determining the at least one quantitative airway information.

The first medical image data can comprise at least a first medical image and/or first metadata of a first medical image. In particular, the first medical image data can be acquired by a medical imaging device like a computed tomography device, a magnet resonance tomography device, a positron-emission tomography device, a single photon emission computed tomography device, a flatfield x-ray device, an ultrasound device, etc. In particular, the first medical image is a medical image of an examination volume, in particular, the examination volume is a subregion of a patient. In particular, the first medical image data can be acquired by a combination of the aforementioned devices. In particular, the first medical image data can comprise a three-dimensional and/or a two-dimensional first medical image.

The first medical image can comprise a plurality of pixels or voxels. In particular, the first medical image comprises a plurality of voxels if it is a three-dimensional medical image, and it comprises a plurality of pixels if it is a two-dimensional medical image. In particular, each pixel or voxel of the plurality of pixels or voxels can comprise a pixel value or voxel value, whereby the pixel value or voxel value comprises information about the tissue imaged in the first medical image at the corresponding position.

In particular, the pixel values or voxel values can comprise intensity values. The intensity values can for example correspond to an x-ray attenuation coefficient and/or be given in Hounsfield units. The first metadata can comprise acquisition parameters for acquiring the first medical image, patient-specific data like the age, the weight, the gender etc. of the patient being subject of the medical image, parameters measured in the first medical image like intensity values in Hounsfield units, the parameters in a magnet resonance image etc.

In particular, the first medical image data can be determined, in particular by the computation unit. The first medical image can be determined based on alternative input data like another medical image or metadata. Exemplarily, the first medical image data can comprise a first medical image, and the first medical image can be a two-dimensional slice which is determined based on a three-dimensional medical image.

The airway segment comprises at least one part of the airways. In particular, the airways comprise at least one of the following of a patient: the trachea, the bronchia, the bronchioles, the alveoli, and combinations and/or substructures thereof. In particular, the airways of the patient branch out into even smaller structures. In particular, an airway segment comprises at least a part of the airways. In particular, the airway segment can comprise a part of the airways of a patient extending between two branching points of the airways. Alternatively, the airway segment can comprise a part of the airways of the patient which is smaller than the part between two branching points of the airways. Alternatively, the airway segment can comprise the airways of the patient as a whole, or any part of the airways of the patient.

In general, the trained function mimics cognitive functions that humans associate with other human minds. In particular, by training based on training data the trained function is able to adapt to new circumstances and to detect and extrapolate patterns.

In general, parameters of the trained function can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, the trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

The output data can comprise processed image data based on the first medical image data. In particular the processed image data can be of the same size as the first medical image data. The processed image data having the same size as the first medical image data means that the processed data is also a medical image of the same dimensionality as the first medical image, and comprising the same number of pixels or voxels with respect to every one of the dimensions.

In particular, the quantitative airway information is related to an airway segment of the airways of a patient, and comprises information about the airway segment. In particular, the airway information can comprise information about geometrical properties of the airway segment. Alternatively or additionally the at least one quantitative airway information can comprise information about an attenuation property of the airway segment. The attenuation property can be based on the intensity values of the plurality of pixel or voxel depicting the airway segment in the first medical image. In particular, the attenuation property depends on the attenuation coefficient of the airway segment. The quantitative airway information can be determined based on the output data of the first trained function. In particular, the at least one quantitative airway information can comprise COPD-related information.

Providing the at least one quantitative airway information can comprise displaying, storing and/or transmitting the at least one quantitative airway information. In particular, providing the at least one quantitative airway information can comprise displaying the at least one quantitative airway information by a monitor. Alternatively or additionally the at least one airway information can be used in further analysis steps.

The inventors recognized that it is advantageous to determine the at least one quantitative airway information based on a first trained function. Compared to a manual determination by a user, using the first trained function allows a faster determination of the at least one airway information. Furthermore, compared to other algorithms known from prior art, in particular, compared to non-learning algorithms, using the first trained function provides less erroneous results than non-learning algorithms. In particular, the inventors recognized that the first trained function furthermore provides a result for the at least one quantitative airway information even for small parts of the airways.

According to a further embodiment of the invention, the first trained function comprises a convolutional neural network.

In particular, the first trained function can comprise a dense unit network. In particular, the dense unit network comprises a convolutional layer, a max pooling layer and a deconvolutional layer. In particular the dense unit network comprises at least two parts: a first part and a second part. In particular, in the first part of the dense unit network the input data is down-sampled. Down-sampled means that the dimension of the input data is reduced. In particular, the number of pixels or voxels of the input data is reduced, in the case that the input data is a medical image. The input data can be the first medical image data. In the second part of the network the down-sampled data is up-sampled again such that the output data comprises has the same format as the input data. In particular, there is a one-to-one correspondence between nodes of the input layers and nodes of the output layers, in particular, also with respect to the numerical values they can represent.

In particular, if the input data is equivalent to the first medical image data, the output data having the same size means that the output data is also a medical image of the same dimensionality as the first medical image, and comprising the same number of pixels or voxels with respect to every one of the dimensions. Furthermore, layers of the dense unit network are concatenated. For example, the last layer can be concatenated with the first layer of the dense unit network. In other words, the last layer can receive information from the first layer. A detailed description of a dense unit network is for example provided by çiçek et al., "3D U-Net: Learning Dense Volumetric Segmentation from Sparse Annotation" (MICCAI, Springer, Vol. 9901: 424-432, 2016), the entire contents of which are hereby incorporated herein by reference.

The inventors recognized that a convolutional neural network, especially a dense unit network, is suited for handling image data. They recognized that the output data can be determined by applying the first trained function, comprising a convolutional network, on the first medical image, which is comprised by the first medical image data.

According to an alternative further embodiment, the first trained function can comprise another machine learning algorithm, for example an arbitrary neural network and/or a random forest algorithm.

The inventors recognized that the other machine learning algorithms can be trained with less training data. They recognized that such machine learning algorithms are especially suited if there is little training data available.

According to a further embodiment, determining the at least one quantitative airway information is performed by a non-learning algorithm.

In particular, a non-learning algorithm is an algorithm that does not depend on a training dataset. In other words, the output data of the first trained function can be used as input data for the non-learning algorithm.

The inventors recognized that no training data is necessary if the at least one quantitative airway information is determined by a non-learning algorithm. Hence, this application is suited for providing at least one quantitative airway information in the case that no training can be performed or if the determination of the at least one airway information is such standardized that it can reasonably be performed by a non-learning algorithm.

According to an alternative further embodiment, determining the at least one quantitative airway information is performed by a further trained function.

The further trained function received the output data of the first trained function as input data.

The inventors recognized that determining the at least one output data by a further trained function can help to accelerate the process of determining the at least one quantitative airway information.

According to an alternative further embodiment, the output data comprises the at least one quantitative airway information of the airway segment.

In particular, the at least one quantitative airway information can be determined by the first trained function.

In particular, the step of determining the at least one quantitative airway information comprises extracting and/or selecting the at least one quantitative airway information of the airway segment from the output data. In particular, the output data can be the at least one quantitative airway information. In particular, in this case extracting and/or selecting the at least one quantitative airway information means using the output data.

The inventors recognized that like this it is possible to determine the at least one quantitative airway information within one step out of the first medical image data. They recognized that like this less data has to be cached between different steps of the method. This helps to save memory space and to accelerate computing processes like applying the first trained function or determining the at least one quantitative airway information.

According to a further embodiment of the invention the output data comprises a mask of a wall of the airway segment.

In particular, the wall of the airway segment can be tubular-shaped and separates the interior of the airway segment from the exterior or the environment. In particular, the interior of the airway segment can comprise breathing air. The wall of the airway is interspersed with blood vessels enabling the gas exchange. In particular, the wall is a three-dimensional object if the first medical image of the airway segment is three-dimension. In particular, the mask of the three-dimensional wall can also be three-dimensional. Alternatively, the mask of the three-dimensional wall can comprise at least one two-dimensional mask e.g. of a cross-section of the three-dimensional wall. If the first medical image of the airway segment is two-dimensional, the wall and thus also the mask are also two-dimensional.

In particular, the medical image data can comprise at least a first medical image.

In particular, the mask can be related to the pixel values respectively voxel values of the first medical image. With other words, the mask can be in relation with the intensity values of the pixels or voxels of the first medical image.

The inventors recognized that the mask is suitable for segmenting the airway wall. They recognized that the geometrical properties described by the wall are good indicators for the state of COPD. They recognized that the mask is suitable for determining the at least one quantitative airway information. They furthermore recognized that the mask is suitable for investigating at least a geometrical property of the airway segment. The inventors recognized that it is advantageous to determine the mask by applying the first trained function. This allows a segmentation of the wall with a similar quality as manual segmentation but much faster. In particular, a physician does not need to segment the wall by hand. This saves cost and time and enables the physician to concentrate on more specific tasks which cannot as easily be replaced by a learning network. In particular, under some circumstances the segmentation of the wall can be less erroneous if it is performed by the first trained function than for example by an inexperienced physician.

According to a further embodiment, the mask is a binary mask of the wall of the airway segment.

In particular, the mask is of the same size as the first medical image. In particular, the mask having the same size as the first medical image means that the mask is also a medical image of the same dimensionality as the first medical image, and comprising the same number of pixels or voxels with respect to every one of the dimensions. In particular, the pixel or voxel values of the mask can comprise a '1' or 'True' for pixels or voxels that represent the wall within the medical image and a '0' or 'False' elsewhere. Alternatively, the pixel values or voxel values of the mask can comprise a '0' or 'False' for pixels or voxels that represent the wall within the medical image and a '1' or 'True' elsewhere.

The inventors recognized that a binary mask of the wall comprises all information for extracting the geometrical properties of the wall. In particular, a binary mask does not comprise information which is not necessary in relation to the geometrical properties. This saves memory space. In particular, they recognized that the geometrical properties of the wall can easily be extracted based on a binary mask of the wall.

According to an alternative embodiment of the invention, the mask comprises additional information about the density of the wall.

The density of the wall can for example be the radiographic density. With other words, the density of the wall can be related to the x-ray attenuation of the wall. The information about the density of the wall can be encoded in intensity values of pixels or voxels within an image of the mask. The information about the density of the wall can for example be based on the Hounsfield unit of the intensity values of the pixels or voxels corresponding to the wall or on further quantitative information based on the first medical image data.

The inventors recognized that the information about the density of the wall can be used in addition to the geometrical properties of the wall. They recognized that information about the density can comprise information about changes of the structure of the tissue of the wall of the airway segment. Changes of the tissue can help to diagnose further lung diseases and/or COPD.

According to a further embodiment, the mask is based on a two-dimensional projection of the airway segment if the first medical image of the airway segment is determined based on a three-dimensional medical image.

In other words, the first medical image of the airway segment can be a two-dimensional projection of the airway segment along a direction of the projection. The mask can then be determined in the two-dimensional projection of the airway segment. In particular, the mask can comprise a binarization of the two-dimensional projection of the airway segment.

The inventors recognized that it is advantageous to determine the mask of the wall within a two-dimensional projection of the airway wall. They recognized that errors can be reduced by determining the mask based on the two-dimensional projection because the wall thickness of the projection is comparable to a mean of a plurality of wall thicknesses along the projected airway wall segment. Furthermore, they recognized that it saves computation time if the mask is determined for the two-dimensional projection of the airway wall instead of determining a plurality of masks along the airway segment. In particular, a physician can only consider a limited number of data for diagnosing a patient. The inventors recognized that it is not necessary to provide more data than it can be analyzed by the physician.

According to a further possible embodiment, in the case that the first medical image is a three-dimensional medical image, the mask can comprise at least one sub-mask of a two-dimensional projection of at least a sub-segment of the airway segment.

The sub-segment comprises at least a part of the airway segment. In other words, the airway segment can be divided up into smaller parts, called sub-segments. For each of the sub-segments a two-dimensional projection can be determined. For each two-dimensional projection a two-dimensional mask can be determined. In other words, the wall of a three-dimensional first medical image of the airway segment can be described by a plurality of sub-masks.

The inventors recognized that for a curved airway segment it is advantageous to determine a plurality of sub-masks for a plurality of two-dimensional projections of sub-segments of the airway segment. They recognized that a two-dimensional projection of a curved airway segment can cause a blurred wall within the two-dimensional projection of the airway segment. Hence, they recognized that it is advantageous to divide the curved airway segment up into smaller sub-segments. The curvature of each sub-segment should be negligible.

According to an alternative embodiment, the mask is a three-dimensional mask based on the first medical image data, wherein the first medical image data comprises a three-dimensional first medical image.

The inventors recognized that a three-dimensional mask comprises all geometrical information of the airway wall without approximations. They recognized furthermore that a vivid illustration of the airway wall can be provided to the user if the mask is three-dimensional.

According to an embodiment of the invention, the at least one quantitative airway information relates to the wall thickness of the airway segment.

In particular, the at least one quantitative airway information can comprise at least one value describing the wall thickness of the airway segment. The value describing the wall thickness is subsequently called wall thickness.

In particular, the wall of the airway segment can be tubular shaped. A centerline segment of the airway segment can be arranged parallel to the tube. In particular, the centerline segment is arranged parallel to the longitudinal axis of the tube. In particular, the airway wall segment can be extended along the centerline segment in a three-dimensional image. Advantageously, the centerline segment is located at the center of the airway segment. In particular, for a curved airway segment, the centerline segment shows the same curvature as the airway segment.

In particular, the wall thickness can be determined within a plane approximately perpendicular to the centerline segment of the airway segment. Like this, it can be ensured that no perspective distortions have an influence onto the determined wall thickness.

The wall of the airway segment in a two-dimensional image can be circular or oval shaped, whereby the two-dimensional image can be a cross-section of the airway segment. In this case, the centerline segment intersects the two-dimensional image at a point. This point is situated within the center of the two-dimensional projection of the airway segment. In other words, this point is situated in the center of the circle or ellipse described by the wall of the airway segment.

In particular, the wall thickness can be determined along a ray-like line starting at the centerline segment and being approximately perpendicular to the centerline segment. Hence, the line intersects the wall. The wall thickness can be determined in relation to this line.

In particular, the wall thickness of the airway segment can be determined based on the output data of the first trained function, in particular based on a non-learning algorithm.

In particular, the wall thickness can be determined based on the mask of the wall of the airway segment. For a binary mask the wall thickness can e.g. be the sum over the pixel values along a line or path which is perpendicular to the wall.

The inventors recognized that the wall thickness value is an important indicator for COPD assessment.

According to a further embodiment, the quantitative airway information can comprise a first plurality of wall thickness values.

In particular, all wall thickness values are determined approximately perpendicular to the centerline segment. In particular, the first plurality of wall thickness values can be determined for a plurality of rotation angles with respect to the centerline segment.

The inventors recognized that it is advantageous to determine a first plurality of wall thickness values for a plurality of rotation angles with regard to the centerline segment. They recognized that the wall thickness can vary for different rotation angles with respect to the centerline segment.

According to a further embodiment, the at least one quantitative airway information comprises the mean or the median of the first plurality of wall thickness values.

The inventors recognized that determining the median value of a plurality of wall thickness values reduces the influence of outliers.

According to a further possible embodiment of the invention, the wall thickness of a fixed rotation angle can be determined as a mean value or a median value of a second plurality of wall thickness values comprising at least two wall thickness values for two points at the centerline segment.

In other words, the second plurality of wall thickness values comprises at least two wall thickness values, which are determined for the same rotation angle at two different positions along the centerline segment of the airway segment.

In particular, the at least one airway information can comprise the second plurality of wall thickness values, if the first medical image is a three-dimensional image. The number of wall thickness values in the second plurality of wall thickness values depends on a sampling or on an interpolation of the three-dimensional medical image along the centerline segment. The sampling depends on a size of the voxel. The interpolation can be performed to calculate values in between two voxel values.

In particular, a second plurality of wall thickness values for each rotation angle of the wall thickness values of the first plurality can be determined.

In particular, the quantitative airway information can comprise the mean value or the median value of the combination of the first and second plurality of wall thickness values.

The inventors recognized that determining a second plurality of wall thickness values for different positions along the centerline segment helps to avoid distortions due to a curvature of the airway segment, especially for a three-dimensional first medical image of the airway segment. In particular, they recognized that computing the mean or the median of the first and/or second plurality of wall thickness values reduces the influence of outliers.

According to a further embodiment, a summarized wall thickness value of the fixed rotation angle can be determined based on a plurality of output data.

The plurality of output data can be determined for a plurality first medical image data of a plurality of airway segments. The summarized wall thickness value can be comprised by the quantitative airway information. Alternatively, the summarized wall thickness value of the fixed angle can be determined based on a plurality of quantitative airway information related to the plurality of first medical image data. In particular, the summarized wall thickness value can be the mean value or the median value of a third plurality of wall thickness values. Each wall thickness value of the third plurality of wall thickness values can be determined in relation to a first medical image data of a plurality of first medical image data.

The inventors recognized that the summarized wall thickness value can help a physician to get a fast overview of the wall thickness of a larger part of the airways. This helps the physician to provide a fast diagnosis for COPD.

According to a further embodiment of the invention, the quantitative airway information comprises at least one of:
 a wall thickness of the airway segment,
 a lumen radius of the airway segment,
 an outer wall radius of the airway segment, and
 a wall percentage of the airway segment.

In particular, this quantitative airway information can be determined in the manner as described above for the wall thickness value.

The lumen radius is the radius of the inner wall of the airway wall. The wall percentage describes the proportion of the airways (the tube), including the hollow inner area, that is covered by the airway wall.

In particular, the quantitative airway information can comprise a plurality of values of at least one of:
 wall thicknesses of the airway segment,
 lumen radius of the airway segment,
 outer wall radius of the airway segment, and
 wall percentages of the airway segment.

In particular, the plurality of values can be determined for a plurality of rotation angles of the airway segment with regard to the centerline segment of the airway segment.

The inventors recognized that these features can be determined with the first trained function. Furthermore, they recognized that like this a standardized method for determining at least one of the above-mentioned features can be provided. They recognized that this improves the comparability of examinations of a patient or between different patients.

According to a further embodiment of the invention, the method furthermore comprises the step of determining a classification value of a COPD state based on the quantitative airway information.

In particular, the classification value can be related to the type and/or severity of the COPD for a certain patient. In particular, the classification value relates to the association of a patient with at least one of at least two categories of COPD (a synonym is "state of COPD"). These categories may be for example "COPD" and "no COPD", or "strong COPD", "intermediate COPD" and "no COPD", wherein strong and intermediate relate to states of COPD.

Alternatively, the categories can relate to clinical defined states of COPD.

The classification value can be based on the wall thickness value respectively the first and/or second and/or third plurality of wall thickness values of the airway segment. The classification can be based on thresholds of the wall thickness respectively the mean value or the median value of the wall thickness in relation to a plurality of airway segments. Such thresholds can be provided by tables. The threshold can depend on the diameter of the airway segment. In particular, as smaller the diameter of the airway segment as smaller the threshold of the wall thickness.

The inventors recognized that providing the classification value helps a physician like a radiologist or a pulmonologist to diagnose COPD in an early state. Furthermore, the classification value can help the physician to provide an adapted therapy for the patient. Additionally, the classification value provides the physician a quick overview over the state of the COPD without going into detail. The physician can decide if further examinations are necessary. The inventors furthermore recognized that the classification related to the output data of the first trained function provides a faster and more reliable information about the COPD state of a patient than previous manual or non-learning techniques like FWHM.

According to a further embodiment of the invention, the first medical image data is extracted from a second medical image data, wherein the first medical image data is two-dimensional, and the second medical image data is three-dimensional.

In particular, the first medical image data is two-dimensional if it comprises a two-dimensional first medical image, and the second medical image data is three-dimensional if it comprises a three-dimensional medical image. In particular, the second medical image data comprises a second medical image depicting at least the airway segment, a whole lung of the patient and/or a part of the whole lung of the patient. In particular, the lung comprises the airways. In particular, the second medical image data comprises a plurality of voxels.

Each voxel comprises an intensity value which is related to properties of the tissue represented by the voxel.

In particular, the second medical image can be acquired by a medical imaging device, in particular by an x-ray device (e.g. a computed tomography device or a c-arm x-ray device), a magnet resonance tomography device, a positron-emission tomography device, a single photon emission computed tomography device, etc. In particular, the second medical image can be acquired by a combination thereof.

In particular, the second medical image can be acquired by a medical imaging examination based on x-rays (e.g. a computed tomography examination and/or an examination with a c-arm).

In particular, the first medical image can for example be a slice of the second medical image. Alternatively, the first medical image can be a two-dimensional projection of a part respectively a section of the second medical image. The part respectively section of the second medical image can for example be a segmented part of the lung or a plurality of slices which are acquired during computed tomographic reconstructions.

The inventors recognized that it is advantageous to provide two-dimensional medical image data to the first trained function. They recognized that this reduces computing time compared to providing three-dimensional medical data, because the number of input and output variable is smaller. Furthermore, a larger amount of two-dimensional training data is available because based on a single three-dimensional imaging training data set a plurality of two-dimensional imaging training data sets can be determined and used as input training data for training the first trained function.

According to a further embodiment of the invention, the method furthermore comprises receiving the second medical image data, applying a second trained function to the second medical image data, wherein an airway probability map is generated, and applying a skeletonization algorithm on the airway probability map determining an airway centerline tree, wherein the first medical image data is determined based on the airway centerline tree and the second medical image data.

In particular the second medical image data comprises a second medical image depicting at least a part of the lung and/or the trachea. In particular, the second medical image is a three-dimensional image. The lung comprises the airways apart of the trachea. The second medical image comprises at least the airway segment.

The airway probability map is based on the second medical image data providing information about the occurrence of airways within the second medical image data. In particular, the airway probability map provides a probability value for each voxel within the second medical image data. The probability value corresponds to the probability that the respective voxel relates to a part of the airways imaged by the second medical image. In particular, the airway probability map can be interpreted as a three-dimensional image, wherein the size of the airway probability map in terms of voxels with respect to every one of the dimensions equals the size of the second medical image with respect to said dimension.

In particular, the airways can be depicted within the probability map starting at the trachea and ending at the alveoli.

In particular, the airway probability map can be a three-dimensional representation of the airways in the second medical image. In particular, the airway probability map can comprise connected one-dimensional structures within a three-dimensional image. In other words, the dimension with respect to the voxels depicting the airways in the second medical image can be equal to the dimension of the voxels within the airway probability map depicting the occurrence of the airways within the first medical image.

The skeletonization algorithm serves to determine the centerline tree of the airways respectively the airway segment within the second medical image. The airway centerline tree can be calculated by applying the skeletonization algorithm to the airway probability map.

In particular, the skeletonization algorithm can be configured to ensure a curved smoothness and/or connectivity of the airway centerline tree, and can deal with background noise. Curved smoothness means that the airway centerline tree follows the organic structure of the airways. Connectivity means that the airway centerline tree comprises no gaps within the airways depicted in the second medical image. The connectivity of the airways is always given in a human being to enable the air flow. Dealing with background noise means that the skeletonization algorithm recognizes that noise does not correspond to the airways.

A skeletonization algorithm with these properties can e.g. be based on an adaption of the Rivulet algorithm. Such an adaption is described by Siqi et al. ("Automated 3-D Neuron Tracing With Precise Branch Erasing and Confidence Controlled Back Tracking", IEEE Transactions on Medical Imaging, Vol. 37, No. 11: 2441-2452, 2018), the entire contents of which are hereby incorporated herein by reference.

The airway centerline tree relates to the course of the airways or at least of the airway segment. The airways comprise at least one airway segment. The airway centerline tree comprises at least the centerline segment of the airway segment. The centerline is located in the center of the airways. In other words, the airway centerline follows the center of the tubular-shaped airways. In particular, the airway centerline tree can be a three-dimensional representation of the airways within the second medical image.

In particular, the pixel intensities of the first medical image are based on the voxel intensities of the second medical image. In particular, the first medical image comprises at least a part of the voxel intensities of the second medical image as pixel intensities. Advantageously, the first medical image comprises a part and/or a slice of the second medical image. The location of the part and/or slice within the second medical image data can be determined in relation to the airway centerline tree. The part and/or slice comprises at least a depiction of the airway segment.

The inventors recognized that calculating the airway centerline tree provides information about the course of the airways. They recognized that this enables to determine the first medical image data in relation to the course of the airways respectively of the airway segment. In particular, they recognized that the first medical image can be automatically determined out of the second medical image with the knowledge of the airway centerline tree. In particular, they recognized that the automatic determination of the first medical image allows in combination with applying the first trained function a full automated provision of the quantitative airway information.

The inventors recognized that a standard segmentation of the airways based on a thresholding of the intensity values of the voxels of the second medical image is difficult to perform because the contrast of the airways to the surrounding tissue is very week. They recognized that the second trained function provides the probability map which takes uncertainties of determining the airway within the second medical image into account.

According to a further embodiment of the invention the airway segment is centered in the first medical image.

In particular, the airway centerline segment related to the airway segment intersects the plane of the first medical image in the center of the first medical image.

The inventors recognized that it simplifies and accelerates further analysis of the first medical image if the airway segment is centered within the first medical image.

According to a further embodiment of the invention the first medical image data is a slice of the second medical image data, wherein the slice is orthogonal with respect to a part of the airway centerline tree corresponding to the at least one airway segment.

In particular the slice comprises a cross-section of the airway segment. The airway segment can be a subsection of the airways depicted in the second medical image data. The subsection of the second medical image data can be extended along a centerline segment of the airway segment which is imaged in the slice. The centerline segment of the airway segment is part of the airway centerline tree. The airway segment is projected onto the slice along the centerline segment. In other words, the centerline segment is arranged orthogonal onto the plane of the first medical image. In particular, the airway segment can preferably be extended approximately 7 mm along the airway centerline segment.

Alternatively, the airway segment which is projected onto the slice can be extended from one branching point of the airway segment to the next branching point. In particular, in this context the airway centerline segment of the projected airway segment should be uncurved. If the airway centerline segment is curved within the airway segment it should be further subdivided in sub-segments within which the curvature of the airway centerline sub-segment can be neglected. These sub-segments can then be projected onto slices. Like this, distortions due to the projection can be avoided.

In particular, the slice is orthogonal with respect to a part of the airway centerline tree corresponding to the at least one airway segment. In other words, the part of the airway centerline tree corresponding to the at least one airway segment, the airway centerline segment, is arranged orthogonal to an image plane of the first medical image. The image plane respectively projection plane of the first medical image is the plane of the slice of the first medical image. Due to the orthogonality of the centerline segment onto the plane of the first medical image the cross-section of the airway segment is preferably circular shaped.

The inventors recognized that the first medical image data advantageously comprises a cross-section of the airway segment. They recognized that the cross-section is advantageously perpendicular to the course respectively the centerline segment of the airway segment. Like this, distortions which cause an adulterated wall thickness value can be minimized. In particular, the evaluation of the geometrical properties of the airway segment can be accelerated by providing a cross-section which is perpendicular to the airway centerline segment of the airway segment.

Furthermore, the inventors recognized that like this a fully automated COPD-related examination can be provided. The airway centerline tree can automatically be determined based on the three-dimensional medical image data. Based on the airway centerline tree, at least one two-dimensional first medical image data can automatically be determined. This two-dimensional first medical image data can be used as input data for automatically determining the mask of the airway wall. This mask can be used to automatically determine the at least one quantitative airway information and, in particular, a classification value. Hence, no user input is necessary apart of acquiring the second medical image data.

In a second embodiment, the invention relates to a computer implemented method for providing a first trained function. The method comprises receiving first medical image data of a first airway segment, receiving first annotated data, wherein the first annotated data is based on the first medical image data, wherein the first annotated data is a mask of a wall of the airway segment, training the first trained function based on the first medical image data and the first annotated data, and providing the first trained function.

In particular, the first annotated data is determined by annotating the first medical image data.

The first trained function can be trained by providing a plurality of first medical image data as input training data and the corresponding first annotated data as output training data.

In particular, the annotation can be performed by a skilled person like a radiologist. In particular, the skilled person can manually annotate the wall of the airway segment within the first medical image. In particular, the skilled person provides a mask of the wall of the airway segment based on the first medical image data.

In particular, this manually annotated data serves as training output data for training the first trained function.

The inventors recognized that manually annotated data are the most precise way for annotating data.

According to a further embodiment of the invention the method for providing the first trained function additionally comprises receiving first pre-training medical image data of a second airway segment, determining a pre-training mask of a wall of the airway segment based on a first deterministic algorithm, pre-training the function based on the first pre-training medical image data and the pre-training mask.

In particular, the first pre-training medical image data is a pre-training input training data and the pre-training mask is a pre-training output training data.

In particular, the training related to the training with the pre-training input and the pre-training output training data is performed before training with the manually first annotated data as output training data.

In particular, the first deterministic algorithm is appropriate for automatically annotating the first pre-training medical image data. In particular, the deterministic algorithm can be applied to determine the pre-training mask of the wall of the airway segment of the first pre-training medical image data. In particular, the first pre-training medical image data can be the first medical image data. In other words, the first airway segment can be the second airway segment.

The inventors recognized that by annotating the first pre-training medical image data with a first deterministic algorithm a larger amount of training data can be provided for training the trained function than by manual annotation. They recognized that the automatically annotated data is more error-prone than the first annotated data which is preferably manually annotated. They recognized that the automatically annotated data can be used for pre-training the first trained function in a first training step. In a second training step the first annotated data can be used for fine-tuning the trained function. The inventors recognized the advantage that by separating the training procedure in two steps the amount of training data can be increased without the need of a huge amount of manually annotated data.

According to a further embodiment of the invention the first deterministic algorithm is based on a Full-Width-Half-Maximum Segmentation.

In particular, the deterministic algorithm determines the pre-training mask based on the pixel or voxel values, respectively intensity values of the first pre-training medical image data. The deterministic algorithm determines the change of the pixel or voxel values across the wall of the airway segment and the surrounding tissue. A line-plot respectively ray of the pixel or voxel values approximately perpendicular to the wall of the airway segment and to the centerline segment corresponding to the airway segment comprises an extremum, in particular, a maximum or a minimum.

According to the "Full Width Half Maximum" two points with respect to the extremum on the smooth curve can be determined. One of these points is located on the left and the other point on the right of the extremum. The plurality of pixels or voxels in the part in between the two points can be segmented as wall of the airway segment. This plurality of pixels or voxels can be called segmented plurality. A detailed description of the method can for example be found in Reinhardt et al. (Accurate measurement of intrathoracic airways. IEEE transactions on medical imaging, 16(6), pp. 820-827, 1997), the entore contents of which are hereby incorporated herein by reference.

The segmented plurality of pixels or voxels can, in particular, be annotated as '1' or 'True'. Alternatively, the segmented plurality of pixels or voxels can be annotated as '0' or 'False'. This procedure can be repeated for a plurality of line-plots to segment the whole wall of the airway segment. Advantageously, the line-plots cover the whole wall of the airway segment in a ray-like manner. The pixels or voxels which are not part of the segmented plurality of pixels or voxels can be annotated by a '0' or 'False' if the segmented plurality of pixels or voxels is annotated by a '1' or 'True'. Alternatively, they can be annotated by a '1' or 'True' if the segmented plurality of pixels or voxels is annotated by a '0' or 'False'. The result of the deterministic algorithm is the pre-training mask of the wall of the airway segment.

The deterministic algorithm is based on the intensity values. It cannot distinguish between objects within the first pre-training medical image which cause similar intensity values. Hence, for example the deterministic algorithm cannot distinguish between blood vessels which are in direct contact with the wall of the airway segment and the wall itself if both show similar intensity values.

The inventors recognized that the pre-training mask can be determined by the known "Full Width Half Maximum" method. They recognized that the uncertainties of the first trained function due to this simple, error-prone segmentation method based on "Full Width Half Maximum" can be corrected by a follow-up or fine-tuning training with manually annotated data.

In a third embodiment, the invention relates to a first providing system for providing quantitative airway information. The first providing system comprises an interface and a computation unit, wherein the interface and/or the computation unit are configured for receiving and/or determining first medical image data of an airway segment, wherein the computation unit is furthermore configured for applying a first trained function to the first medical image data, wherein output data is generated, wherein the computation unit is furthermore configured for determining the at least one quantitative airway information of the airway segment based on the output data, wherein the interface is furthermore configured for providing the at least one quantitative airway information.

In particular, the first providing system can be configured to execute the previously described method for providing at least one airway information. The first providing system is configured to execute this method and its aspects by the first and second interface and the computation unit being configured to execute the corresponding method steps. In particular, the interface can comprise one or more sub-interfaces. In particular, the computation unit can comprise one or more computation sub-units.

In a further embodiment, the invention relates to a training providing system for providing a first trained function. The training providing system comprises a training interface and a training computation unit. The training interface is configured for receiving first medical image data of a first airway segment. The training interface is furthermore configured for receiving first annotated data, wherein the first annotated data is based on the first medical image data, wherein the first annotated data is a mask of a wall of the airway segment. The training computation unit is configured for training the first trained function based on the first medical image data and the first annotated data. The training interface is furthermore configured for providing the first trained function.

In a fourth embodiment, the invention relates to a computer program product with a computer program and a computer-readable medium. A mainly software-based implementation has the advantage that even previously used first providing systems can be easily upgraded by a software update in order to work in the manner described. In addition to the computer program, such a computer program product can optionally include additional components such as documentation and/or additional components, as well as hardware components such as e.g. hardware keys (dongles etc.) for using the software.

In a further embodiment, the invention relates to a computer program product comprising program elements directly loadable into a memory unit of a first providing system, which induces the first providing system to execute the method according to the claimed method and its embodiments when the program elements are executed by the first providing system.

In a fifth embodiment, the invention relates to a computer-readable storage medium comprising program elements which are readable and executable by a first providing system, to execute the claimed method and its embodiments, when the program elements are executed by the first providing system.

In a further embodiment, the invention relates to a computer-readable storage medium, comprising a first trained function as of at least one embodiment.

The following clauses are also part of the disclosure:

Clause 1: A first training system for providing a first trained function, comprising a first training interface and a first training computation unit, wherein the first training interface and/or the first training computation unit are configured for receiving and/or determining first medical image data of an airway segment, wherein the first training interface is furthermore configured for receiving an output data, wherein the first medical image data of the airway segment is related to the output data, wherein the first training computation unit is configured for training the first trained function based on the first medical image data of an airway segment and the output data, wherein the first training interface is furthermore configured for providing the first trained function.

In particular the first training interface can comprise one or more first training interfaces. In particular, the first training computation unit can comprise one or more first training computation units.

Clause 2: A computer program product comprising a computer program that is directly loadable into a storage of a first training system, which comprises program elements for performing steps of the previously described methods and their embodiments, when the program elements are executed by the first training system.

Clause 3: A computer-readable storage medium comprising program elements which are readable and executable by a first training system, to execute the method of the previously described methods and their embodiments, when the program elements are executed by the first training system.

Clause 4: A computer implemented method for providing a second trained function comprising:
  receiving second medical image data of at least a part of a first airway,
  receiving second annotated data, wherein the second annotated data is based on the second medical image data, wherein the second annotated data is an airway probability map,
  training the second trained function based on the second medical image data and the second annotated data, and
  providing the second trained function.

In particular, the second medical image data can be a three-dimensional medical image of at least a part of the first airway respectively of at least the airway segment. In particular, the second annotated data can be determined by annotating the second medical image data. In particular, the second medical image data can be manually annotated by a skilled person.

The inventors recognized that manually annotating the second medical image data provides high quality and little erroneous annotated data.

Clause 5: Method according to Clause 4 furthermore comprising:
  receiving second pre-training medical image data of at least a part of a second airway,
  determining a pre-training airway probability map based on a second deterministic algorithm, wherein the second deterministic algorithm is based on a morphology-based segmentation,
  pre-training the function based on the second pre-training medical image data and the pre-training airway probability map.

In particular, the second pre-training medical image data can be the second medical image data. In other words, the at least one part of the first airway can be the at least one part of the second airway. In particular, the morphology-based segmentation for determining the pre-training airway probability map is known by a skilled person.

Example algorithms which can be used as the second deterministic algorithm are for example described by Irving et al. (3D segmentation of the airway tree using a morphology based method, Proceedings of 2nd International Workshop on Pulmonary Image Analysis, p. 297-307, 2009), Feuerstein et al. (Adaptive Branch Tracing and Image Sharpening for Airway Tree Extraction in 3-D Chest CT, Proceedings of 2nd International Workshop on Pulmonary Image Analysis, p. 273-284, 2009), Lo et al. (Multiscale Vessel-guided Airway Tree Segmentation, Proceedings of 2nd International Workshop on Pulmonary Image Analysis, p. 323-332, 2009), and Bauer et al. (Airway Tree Reconstruction Based on Tube Detection, Proceedings of 2nd International Workshop on Pulmonary Image Analysis, p. 203-213 2009), the entire contents of each of which are hereby incorporated herein by reference.

In particular, the second pre-training can be applied before training the second trained function with manually second annotated data.

The inventors recognized that even if the pre-training airway probability map is not as precise (especially in the smaller parts of the airway tree) as the manually second annotated data, it can be used for pre-training the second trained function. They recognized that the trained function can be fine-tuned by a second training step using the manually second annotated data. Like this, a huge amount of pre-training airway probability maps can be used for pre-training the second trained function. They recognized that like this it is possible to train respectively fine-tune the second trained function with a small amount of manually second annotated data.

Clause 6: A second providing system, comprising a second interface and a second computation unit,
  wherein the second interface is configured for receiving second medical image data of a first lung,
  wherein the second interface is furthermore configured for providing an airway probability map of the first lung,
  wherein the second computation unit is configured for applying a second trained function to the second medical image data of the first lung, wherein the airway probability map of the first lung is generated.

Clause 7: A second computer program product comprising a computer program that is directly loadable into a storage of a second providing system, which comprises program elements for performing steps of one of the previously described methods and their embodiments when the program elements are executed by the second providing system.

Clause 8: A second computer-readable storage medium comprising program elements which are readable and executable by a second providing system, to execute one of the previously described methods and their embodiments, when the program elements are executed by the providing system.

FIG. 1 displays a schematic flow chart of a first embodiment of the method for providing a quantitative airway information INFO1. The method comprises the steps of receiving REC-1 the first medical image data IMG1 of the airway segment AS1, AS2, applying APP-1 the first trained function for generating the output data, determining DET-2 the at least one quantitative airway information INFO1 based on the output data and providing PROV-1 the at least one quantitative airway information INFO1.

In this embodiment, the first medical image data IMG1 is at least one two-dimensional image of a projection of a cross-section of an airway segment AS1, AS2, which is received by a first providing system in the step of receiving REC-1 the first medical image data IMG1. Advantageously, the projection of the airway segment AS1, AS2 along the centerline segment of the airway segment AS1, AS2 is a projection onto the cross-section of the airway segment AS1, AS2. In a preferred embodiment, the airway segment AS1, AS2 comprises around 7 mm in length along the centerline segment. Receiving REC-1 of the first medical image IMG1 is in particular performed by an interface SYS.IF.

In an alternative embodiment the airway segment AS1, AS2 which is depicted in the first medical image IMG1 comprises a part of the airways of the lung which is extended between two branching points.

In a preferred embodiment a plurality of first medical images IMG1 is received. Advantageously, each first medical image IMG1 of the plurality of first medical images IMG1 depicts a different airway segment AS1, AS2. The plurality of airway segments AS1, AS2 can be a part of the airways respectively at least a part of a lung of a patient. Advantageously, the plurality of airway segments AS1, AS2 forms a whole lung of a patient.

In an alternative embodiment the first medical image data IMG1 is at least a three-dimensional medical image of at least a part of the airways of the lung.

In the step of applying APP-1 the first trained function the output data is generated based on the first medical image data IMG1. In this embodiment, the output data comprises the mask MASK1 of the first medical image IMG1. In the case that a plurality of first medical images IMG1 is received in the previous step a plurality of masks MASK1 is generated by applying APP-1 the first trained function. Advantageously, a mask MASK1 for each first medical image IMG1 of the plurality of medical images IMG1 is generated. In particular, the mask MASK1 is of the same size as the corresponding first medical image IMG1. In particular, the mask MASK1 comprises the same number of pixel respectively voxel as the first medical image IMG1. In particular, the dimensionality regarding the number of pixel or voxel in each dimension correspond in the mask MASK1 and the first medical image IMG1. In this preferred embodiment the mask MASK1 is a binary mask. It comprises a '1' or a 'True' as pixel value or voxel value of the pixel or voxel which depict a part of the wall of the airway segment AS1, AS2 of the first medical image IMG1 and a '0' or 'False' elsewhere. Hence, the mask MASK1 is suitable for segmenting the wall of the airway segment AS1, AS2 in the first medical image IMG1. In alternative embodiments, if the first medical image data IMG1 is three-dimensional, the mask MASK1 is also three-dimensional. Applying APP-1 of the first trained function is in particular performed by a computation unit SYS.CU.

In this embodiment the first trained function comprises an artificial neural network, in particular, a dense unit network. The first trained function is trained in two steps. In a first, pre-training step a set of first pre-training medical images as pre-training input training data and a set of corresponding pre-training masks as pre-training output training data are provided. The pre-training masks can be determined by applying a first deterministic algorithm to the first pre-training medical images. The first deterministic algorithm can comprise a segmentation of the airway wall by applying a Full-Width-Half-Maximum algorithm based on the pixel values of the first pre-training medical images.

In this embodiment the training is performed by a back-propagation algorithm based on a comparison of the result of applying the first trained function to the first pre-training medical training image and the corresponding pre-training mask (e.g., based on the number of pixels or voxels that are wrongly classified). In a second step, the first trained function is fine-tuned. For this purpose, a set of first medical images as pre-training input training data and a set of corresponding first annotated data as pre-training output training data are provided. The set of first annotated data is a set of masks. The masks are determined by a manual annotation of the wall of the airway segment of the corresponding first medical images. The above described training is continued with these data.

As the manual annotation is much more precise, the first trained function which has been trained with the pre-training masks determined with the first deterministic algorithm is fine-tuned. Nevertheless, the determination of pre-training masks with the first deterministic algorithm allows a pre-training with a large set of pre-training masks. Such a number of masks can hardly be determined by manual annotation because the manual annotation is time-consuming.

In the step of determining DET-2 the at least one quantitative airway information INFO1 is determined based on the output data of the previous step. Here, the quantitative airway information INFO1 comprises a value of the wall thickness of the airway wall. In an alternative embodiment, the at least one quantitative airway information INFO1 comprises further geometrical information of the airway segment AS1, AS2 like lumen radius of the airway segment AS1, AS2, outer wall radius of the airway segment AS1, AS2, and wall percentage of the airway segment AS1, AS2. Determining DET-2 the at least one quantitative airway information INFO1 is in particular performed by a computation unit SYS.CU.

In particular, the wall thickness of the airway segment AS1, AS2 is determined based on the mask MASK1 of the airway segment AS1, AS2. In particular, the mask MASK1 of the airway segment AS1, AS2 comprises a projection of a cross-section of the wall of the airway segment AS1, AS2. The wall thickness is determined for a plurality of rotation angles with respect to the centerline segment of the airway segment AS1, AS2. The centerline segment is located at the center of the cross-section and it is perpendicular to an image plane respectively projection plane PJ1, PJ2. The projection plane PJ1, PJ2 is the plane of the first medical image IMG1. In particular, the value of the wall thickness can be a plurality of wall thickness values in relation to the plurality of rotation angles. Alternatively, the value of the wall thickness is the median or mean of the plurality of wall thickness values related to the plurality of rotation angles. In particular, in the case of a plurality of masks MASK1, a wall thickness value can be determined for each of the masks MASK1. A summarized wall thickness value can be determined as the median or the mean of the wall thickness values corresponding to the plurality of masks MASK1 or at least to a part of the plurality of masks MASK1. This summarized wall thickness value can be comprised by the quantitative airway information INFO1.

For a binary mask MASK1, the wall thickness for a given rotation angle with respect to the centerline segment can be determined by integrating along a corresponding line-plot of the mask. The line-plot of the mask is perpendicular to the centerline segment. Advantageously, the line-plot starts at the center of the cross-section and spreads radially towards the wall.

In the step of providing PROV-1 the at least one quantitative airway information INFO1, the information INFO1 is provided. In particular, the at least one quantitative airway information INFO1 can be stored, transmitted, or displayed to a user. For example, the airway segment AS1, AS2 can be shown in a two- or three-dimensional depiction. The walls of the airway segment AS1, AS2 can be depicted colour-coded, wherein the colours code the wall thickness of the corresponding rotation angle of the wall. Alternatively or additionally, the median or mean value of the wall thickness can be provided to the user via an interface. Advantageously, the wall thickness of the plurality of first medical images IMG1 can be depicted in a colour-coded three-dimensional depiction. Providing PROV-1 the at least one quantitative airway information INFO1 is in particular performed by an interface SYS.IF.

Figure 2:
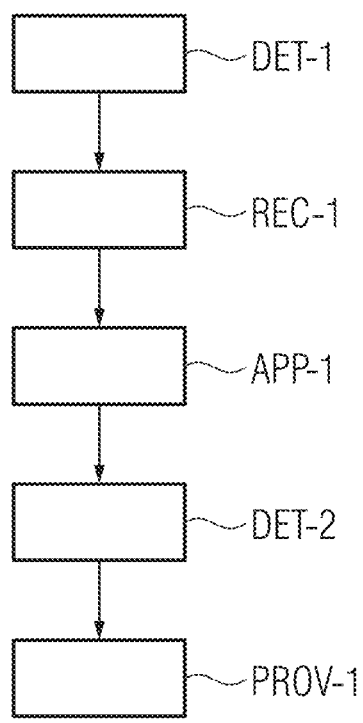

FIG. 2 displays a schematic flow chart of a second embodiment of the method for providing a quantitative airway information INFO1. The steps of receiving REC-1 the first medical image IMG1, applying APP-1 the first trained function, determining DET-2 the at least one quantitative airway information INFO1 and providing PROV-1 the at least one quantitative airway information INFO1 are performed in the same manner as described according to FIG. 1.

In contrast to the embodiment described in FIG. 1, the first medical image data IMG1 is a two-dimensional medical image being based on the second medical image data IMG2. In the step of determining DET-1 first medical image data IMG1, the first medical image data IMG1 is determined based on the second medical image data IMG2. Further details about determining the first medical image data IMG1 based on the second medical image data IMG2 are given in FIG. 6. In this embodiment, the second medical image data IMG2 is a three-dimensional medical image. The three-dimensional medical image is subsequently called second medical image IMG2. In particular, the first medical image IMG1 is a two-dimensional slice of the second medical image IMG2. The first medical image IMG1 depicts the projected cross-section of the airway segment AS1, AS2. The airway segment AS1, AS2 is three-dimensionally depicted in the second medical image IMG2. In this embodiment, the second medical image IMG2 is acquired with a computed tomography device or a C-arm device. Alternatively, the second medical image IMG2 can be acquired by a magnet resonance device, positron emission tomography device, a single photon emission computed tomography device or a combination thereof. Determining DET-1 the first medical image data IMG1 is in particular performed by a computation unit SYS.CU.

Figure 3:
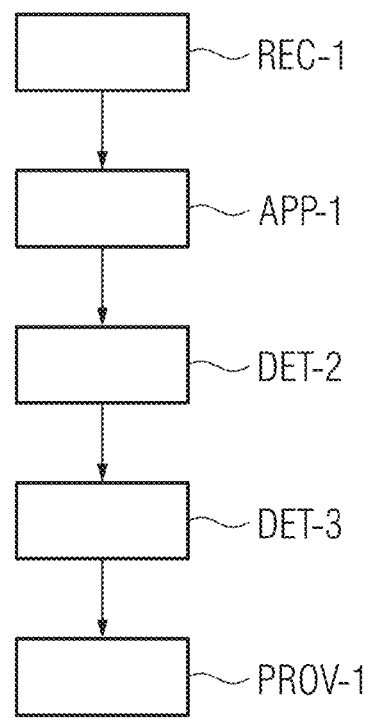

FIG. 3 displays a schematic flow chart of a third embodiment of the method for providing a quantitative airway information INFO1. The steps of receiving REC-1 the first medical image IMG1, applying APP-1 the first trained function, determining DET-2 the at least one quantitative airway information INFO1 and providing PROV-1 the at least one quantitative airway information INFO1 are performed in the same manner as described according to FIG. 1. In an alternative embodiment, the method depicted in this figure can additionally comprise the step of determining DET-1 the first medical image data IMG1 based on the second medical image data IMG2 as described according to FIG. 2.

The step of determining DET-3 a classification value CLASS1 of a COPD state is based on the at least one quantitative airway information INFO1. In particular, the information about the (median or mean) wall thickness of the airway segment can be used for determining a COPD-related classification value CLASS1. The classification value CLASS1 can for example be determined by thresholding, by using tables corresponding to the at least one quantitative airway information INFO1 or by machine learning. In particular, based on the at least one quantitative airway information INFO1, a binary classification can be performed. One of the classification values CLASS1 of the classes can be 'no COPD', the other class can be 'COPD'. These classification values CLASS1 can be provided to a physician. This information can be used by the physician as a basis for deciding about further examinations, diagnosis or therapy. Alternatively, a classification based on the at least one quantitative airway information INFO1 with more than two classes can be determined. For example, a classification based on the clinical classification states of COPD can be determined. This information can also be provided to the physician. Determining DET-3 the classification value CLASS1 is in particular performed by a computation unit SYS.CU.

Figure 4:
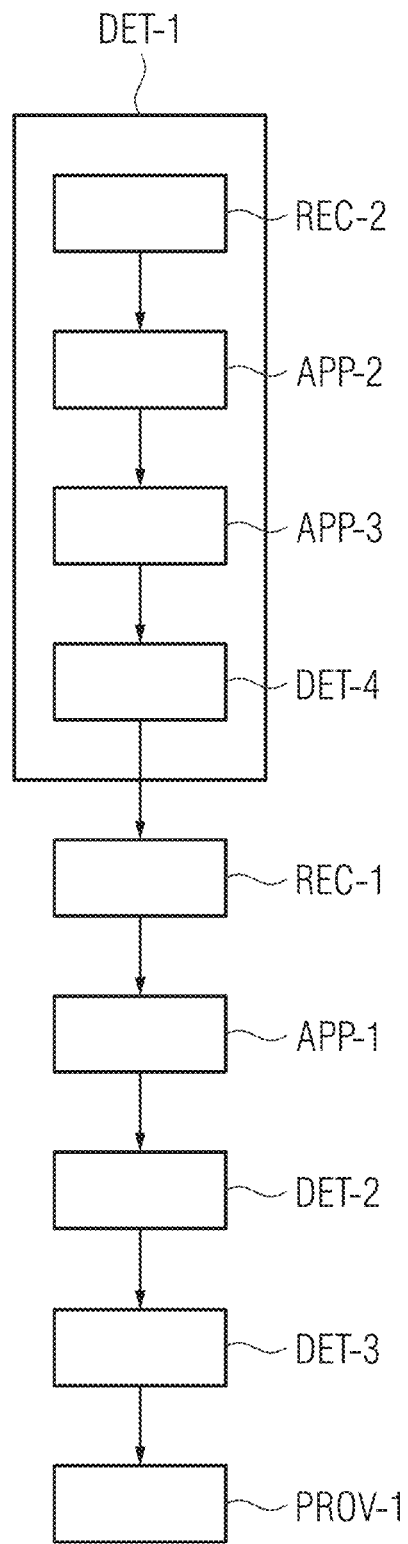

FIG. 4 displays a schematic flow chart of a fourth embodiment of the method for providing a quantitative airway information INFO1. The steps of receiving REC-1 the first medical image IMG1, applying APP-1 the first trained function, determining DET-2 the at least one quantitative airway information INFO1 and providing PROV-1 the at least one quantitative airway information INFO1 are performed in the same manner as described according to FIG. 1. In an alternative embodiment, the method depicted in this figure can additionally comprise the step of determining DET-3 the classification value CLASS1 as described according to FIG. 2.

In contrast to the embodiment described in FIG. 1, within this embodiment the first medical image data IMG1 is a two-dimensional medical image.

The step of determining DET-1 the first medical image data IMG1 comprises the sub-steps of receiving REC-2 the second medical image data IMG2, applying APP-2 a second trained function to the second medical image data IMG2 to determine the airway probability map PROB1, applying APP-3 a skeletonization algorithm to the airway probability map PROB1 for determining the airway centerline tree CTREE1 and determining DET-4 the first medical image data IMG1 based on the second medical image data IMG2 and the airway centerline tree CTREE1.

In the step of receiving REC-2 the second medical image data IMG2, which is a three-dimensional image of at least a part of the lung respectively a part of the airways, is received by the system SYS. The three-dimensional medical image is subsequently called second medical image IMG2. The part of the airways depicted in the second medical image IMG2 comprises at least the airway segment AS1, AS2. In particular, receiving REC-2 the second medical image IMG2 is performed by an interface SYS.IF.

In the step of applying APP-2 the second trained function the airway probability map PROB1 of the part of the airways depicted in the second medical image IMG2 is generated based on the second medical image IMG2. The airway probability map PROB1 provides a probability value for each voxel of the second medical image IMG2, wherein the probability value of a voxel of the airway probability map PROB1 relates to the probability that the said voxel depicts a part of the airways in the corresponding second medical image IMG2. In particular, applying APP-2 the second trained function is performed by a computation unit SYS.CU.

In this embodiment the second trained function comprises an artificial neural network, in particular, a three-dimensional convolutional neural network. Such a network was for example published by Schlemper et al. (Attention-Gated Networks for Improving Ultrasound Scan Plane Detection, 1st Conference on Medical Imaging with Deep Learning (MIDL) 2018, arXiv: 1804:05338v1, 2018). The second trained function is trained in two steps. In a first step a set of second pre-training medical images as pre-training input training data and a set of corresponding pre-training airway probability maps as pre-training output training data are provided. The pre-training airway probability maps can be determined by applying a second deterministic algorithm on the pre-training second medical image data.

Example algorithms which can be used as the second deterministic algorithm are for example described by Irving et al. (3D segmentation of the airway tree using a morphology based method, Proceedings of 2nd International Workshop on Pulmonary Image Analysis, p. 297-307, 2009), Feuerstein et al. (Adaptive Branch Tracing and Image Sharpening for Airway Tree Extraction in 3-D Chest CT, Proceedings of 2nd International Workshop on Pulmonary Image Analysis, p. 273-284, 2009), Lo et al. (Multiscale Vessel-guided Airway Tree Segmentation, Proceedings of 2nd International Workshop on Pulmonary Image Analysis, p. 323-332, 2009), and Bauer et al. (Airway Tree Reconstruction Based on Tube Detection, Proceedings of 2nd International Workshop on Pulmonary Image Analysis, p. 203-213 2009), the entire contents of each of which are hereby incorporated herein by reference.

In this embodiment the pre-training training is performed by a back-propagation algorithm based on a comparison of the result of applying the second trained function to the second pre-training medical image and the corresponding pre-training airway probability map (e.g., based on the number of pixels or voxels that are wrongly classified). In a second step a fine-tuning of the second trained function is performed. For this purpose, a set of fine-tuning second medical images as fine-tuning input training data and a set of corresponding second annotated data as fine-tuning output training data are provided. The second annotated data comprises a set of manually annotated airway probability maps. The manually annotated airway probability maps are determined by manual annotation of the fine-tuning second medical images. With this data the above described training is continued.

In the step of applying APP-3 a skeletonization algorithm, the centerline tree CTREE1 of the airways depicted in the second medical image IMG2 is determined. The skeletonization algorithm is applied on the airway probability map PROB1. The airway centerline tree CTREE1 advantageously provides an information about the course of the airways or at least the part of the airways which is depicted in the second medical image IMG1. The skeletonization algorithm advantageously provides a smoothed and connected airway centerline tree. Additionally, the skeletonization algorithm can handle background noise. In particular, the skeletonization is based on an adapted Rivulet algorithm (Siqi et al., ("Automated 3-D Neuron Tracing With Precise Branch Erasing and Confidence Controlled Back Tracking", IEEE Transactions on Medical Imaging, Vol. 37, No. 11: 2441-2452, 2018), the entire contents of which is hereby incorporated herein by reference. Applying APP-3 the skeletonization algorithm is in particular performed by a computation unit SYS.CU.

In the step of determining DET-4 the first medical image IMG1, the first medical image IMG1 is determined based on the airway centerline tree CTREE1. In particular, the first medical image IMG1 is a two-dimensional slice or at least a two-dimensional part of a slice of the second medical image IMG2. In particular, the centerline segment of the airway segment AS1, AS2 which is depicted in the first medical image IMG1 is perpendicular to the projection of the airway segment AS1, AS2 onto the first medical image IMG1 respectively onto the projection plane PJ1, PJ2. With other words, the airway segment AS1, AS2 is projected along the corresponding part of the airway centerline tree, the centerline segment, on the first medical image IMG1. In particular, the projected cross-section of the airway segment AS1, AS2 is in the center of the first medical image IMG1. In particularly, the centerline segment of the airway segment AS1, AS2 is in the center of the first medical image IMG1. As the centerline segment is arranged perpendicular to the first medical image IMG1, the cross-section should be circular shaped. Determining DET-4 of the first medical image IMG1 is in particular performed by a computation unit SYS.CU.

Figure 5:
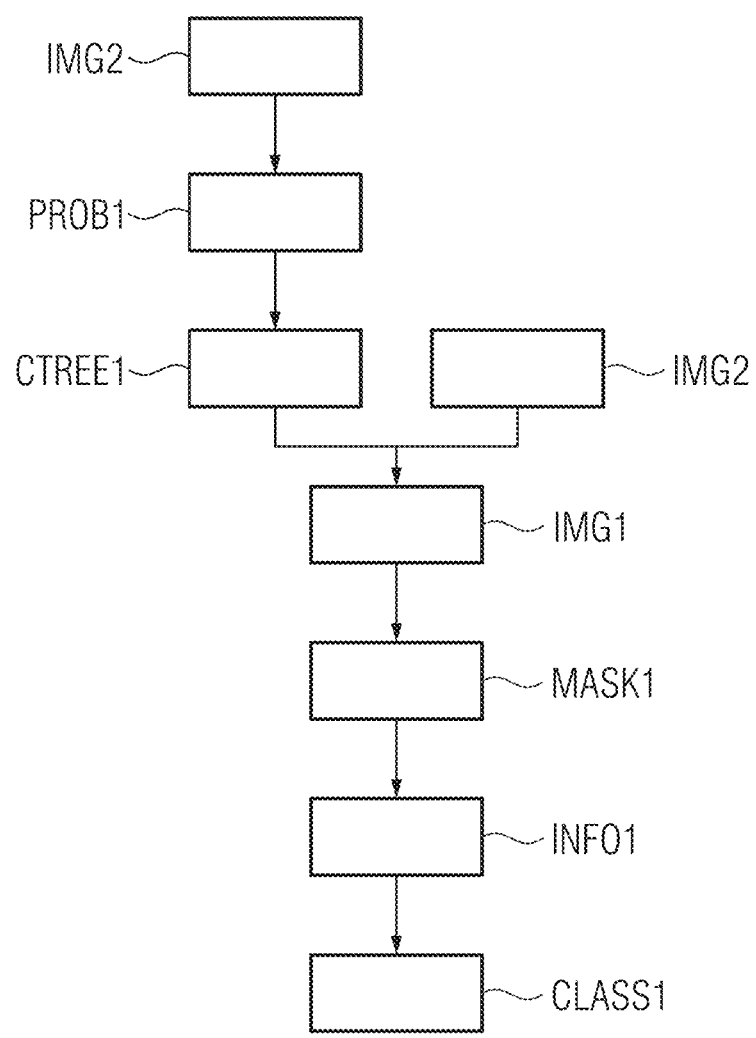

FIG. 5 displays a schematic flow chart of the data according to the fourth embodiment according to FIG. 4.

The second medical image IMG2 is a three-dimensional medical image acquired during a computed tomography examination or an examination with a c-arm. It depicts at least a part of the lung of a patient.

Based on this second medical image IMG2 the airway probability map PROB1 is determined. The airway probability map PROB1 can be interpreted as a three-dimensional image, having the same size (measured in number of voxels) with respect to every dimension as the second medical image IMG2. It follows that the airway probability map PROB1 comprises the same number of voxels as the second medical image IMG2. In particular, there is a one-to-one correspondence between voxels of the second medical image IMG2 and voxels of the airway probability map PROB1. A voxel of the airway probability map PROB1 comprises a probability value which describes the probability that the corresponding voxel of the second medical image IMG2 corresponds to an airway of the lung.

Based on the airway probability map PROB1 the airway centerline tree CTREE1 can be determined. The airway centerline tree CTREE1 is also a three-dimensional image. Within this image voxel with a voxel value of '1' describe the airway centerline. All other voxel values which are outside the airway centerline are set to '0'. The airway centerline tree CTREE1 also has the same number of voxels and the same dimension as the second medical image IMG2. The airway centerline tree CTREE1 is determined by applying an advanced skeletonization algorithm on the airway probability map PROB1. The advanced skeletonization algorithm can be based on the Rivulet algorithm. In addition to conventional skeletonization algorithms it ensures curved smoothness, connectivity and is able to handle background noise.

The airway centerline tree CTREE1 and the second medical image IMG2 are used to determine the first medical image IMG1. For this purpose, an airway segment of the airway centerline tree CTREE1 is determined. The airway segment is extended between two points on the airway centerline tree CTREE1. The corresponding part of the airway centerline tree CTREE1 is called centerline segment. For determining the first medical image IMG1 the airway in the second medical image IMG2 corresponding to the centerline segment is projected along the centerline segment. Hence, the first medical image IMG1 is a two-dimensional projection of the part of the second medical image IMG2 corresponding to the airway segment along the centerline segment. Thus, the first medical image IMG1 depicts a cross-section of the airway segment.

The first medical image IMG1 is used to determine the mask MASK1 of the wall of the two-dimensional projection of the airway segment.

Based on this mask MASK1 the at least one quantitative airway information INFO1 is determined.

The quantitative airway information INFO1 is used to determine the classification value CLASS1. The classification value CLASS1 comprises information about the state of the COPD of the lung depicted in the second medical image IMG2. Alternatively, it can comprise only the information or probability if the patient whose lung is depicted in the second medical image IMG2 suffers from COPD.

Figure 6:
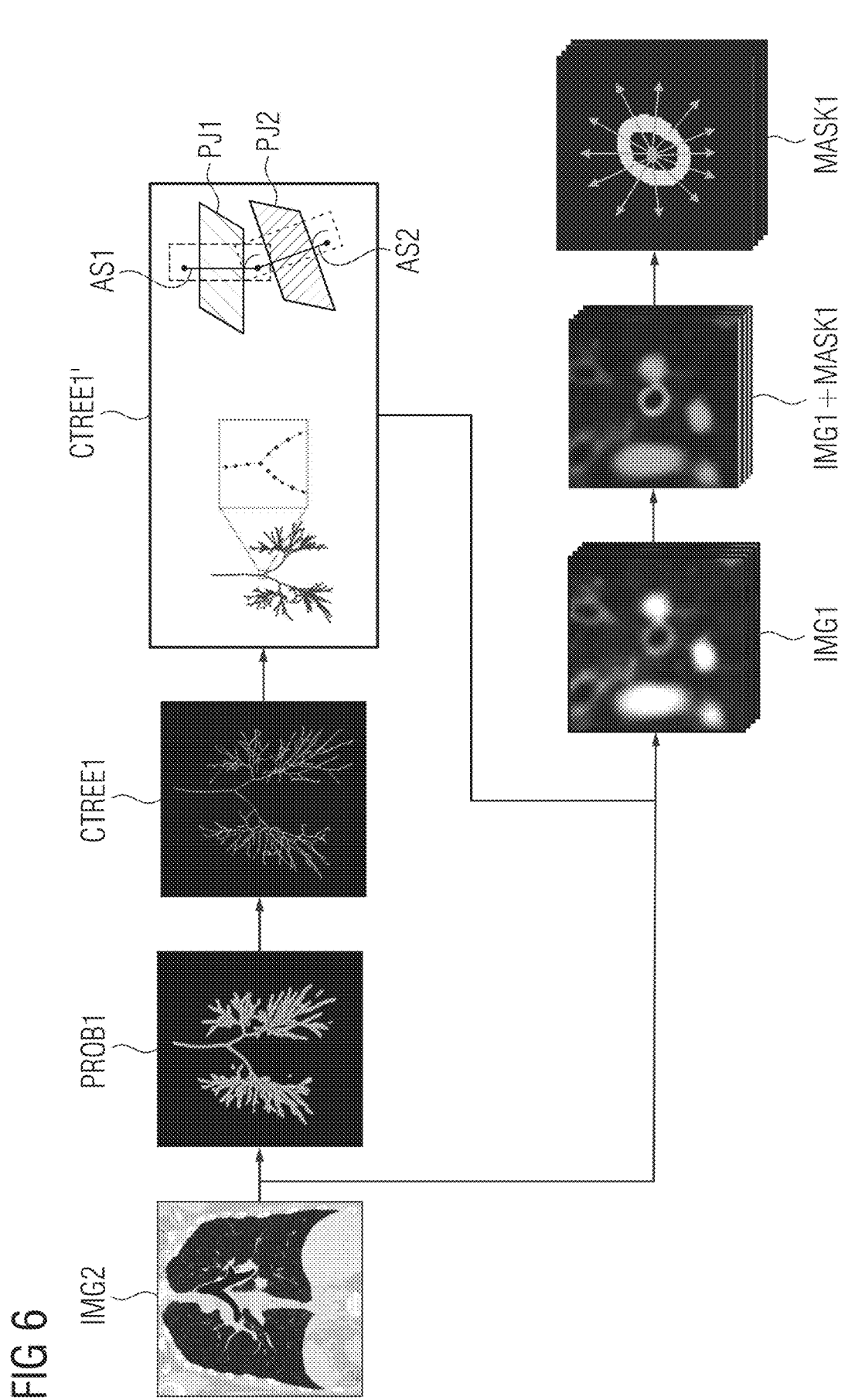

FIG. 6 displays an illustrated flow chart of the data according to FIG. 5, describing in more detail the determination of the airway segment AS1, AS2. It is shown that several points are determined along a negative depiction of the airway centerline tree CTREE1'. A plurality of airway segments AS1, AS2 is determined based on these points along the airway centerline tree CTREE1'. An airway segment AS1, AS2 is extended between two points. In this embodiment the points along the airway centerline tree CTREE1' have a distance of about 7 mm between each other. Alternatively, for example there can be only points at the branching points of the airway centerline tree CTREE1. For a curved centerline segment the points should be closer together. The centerline segment in-between two points can be approximated as being uncurved. Deviations from these approximations will result in the projection of the airway segment AS1, AS2 being blurred. The airway segments AS1, AS2 are projected along the corresponding centerline segment of the airway centerline tree CTREE1 in the projection planes PJ1, PJ2 within the second medical image IMG2. Hereby, the centerline segment of the corresponding airway segment AS1, AS2 is positioned in the center of the projection plane PJ1, PJ2. Like this, a plurality of first medical images IMG1 is determined. For each of the first medical images IMG1 a mask MASK1 of the wall of the two-dimensional projection of the corresponding airway segment AS1, AS2 is determined. A superposition IMG1+MASK1 of a first medical image IMG1 and the corresponding mask MASK1 is depicted in FIG. 6.

Based on the mask MASK1 the first quantitative airway information INFO1 of the corresponding airway segment AS1, AS2 is determined. For a tubular or circular or oval shaped projection of the wall of the airway segment AS1, AS2 a seed point in the center of the tube can be determined.

Advantageously the seed point is located on the corresponding centerline segment of the airway segment AS1, AS2. The seed point serves as center for determining a plurality of wall thickness values. The plurality of wall thickness values is determined for several rotation angles originating at the seed point and being perpendicular to the centerline segment. These rays are depicted as arrows in the figure. In particular the wall thickness corresponding to one ray can be determined by summing up respectively integrating the pixel values of the mask MASK1 along each of the rays, if the mask is a binary mask.

Figure 7:
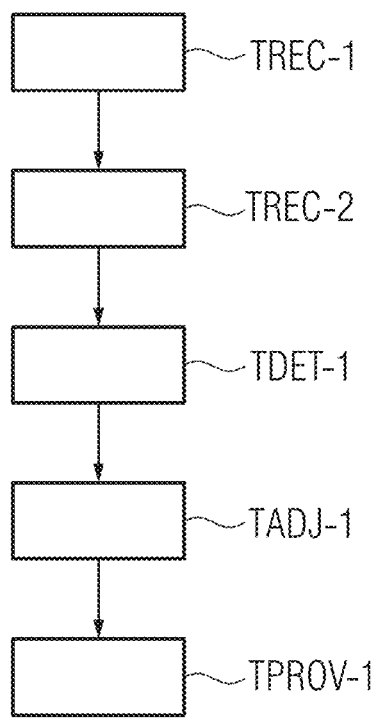

FIG. 7 displays a schematic flow chart of an embodiment of a method for providing a first trained function.

In the first step of receiving TREC-1 a first medical image IMG1 of a first airway segment AS1, AS2 is received. In the second step of receiving TREC-2 a first annotated data is received. The first annotated data is based on the first medical image IMG1. In particular, the first annotated data is a mask of the airway wall of the airway segment depicted in the first medical image IMG1. In particular, the first medical image IMG1 as well as the first annotated data are image data. Both comprise the same number of pixels or voxels, wherein the size of both correspond in each dimension with each other. In particular, receiving TREC-1 the first medical image IMG1 and receiving TREC-2 the first annotated data are performed by a training interface TSYS.IF.

In the next step of determining TDET-1 a mask MASK1 of the airway wall of the airway segment AS1, AS2 depicted in the first medical image IMG1 is determined by applying a first trained function. In particular, the trained function can comprise a neural network. Such a neural network can be a dense unit network. A detailed description of a dense unit network is for example provided by çiçek et al., "3D U-Net: Learning Dense Volumetric Segmentation from Sparse Annotation" (MICCAI, Springer, Vol. 9901: 424-432, 2016), the entire contents of each of which are hereby incorporated herein by reference. In particular, the neural network can comprise nodes and weights.

In particular, the neural network comprises a number of layers. Each layer comprises a number of nodes. The number of nodes of the input layer corresponds to the number of pixel of the first medical image IMG1. The number of nodes of the output layer corresponds to the number of pixel of the mask MASK1. As the mask MASK1 and the first medical image comprise the same number of pixel, in this embodiment, the number of nodes of the input layer is equal to the number of nodes of the output layer.

Alternatively, if the number of pixels is too large, in other words if the necessary memory due to the number of pixel is not available, the first medical image IMG1 can be divided into equally-sized parts. For each part a partial mask is determined. The mask MASK1 can be assembled from the partial masks. In this embodiment, the number of nodes of the input and of the output layer corresponds to the number of pixel of a part of the first medical image IMG1 respectively of a partial mask. Determining TDET-1 the mask is in particular performed by a training computation unit TSYS.CU.

The next step of the displayed embodiment is adjusting TADJ-1 the first trained function. In particular, the determined mask MASK1 is compared to the first annotated data. This comparison can be carried out applying a loss function. Such a loss function can for example comprise calculating an MSE (mean-squared-error). Calculating the MSE comprises summing up the squared pixelwise difference between the mask MASK1 and the annotated data and taking the mean of the sum. Alternatively, the loss function can comprise calculating a BCE (Binary Cross Entropy). These and further possible loss functions are described for example at https://pytorch.org/docs/stable/nn.html#loss-functions, the entire contents of each of which are hereby incorporated herein by reference. In dependence of this comparison the weights of the neural network are adjusted in order to minimize the difference between the determined mask and the annotated data. In particular, this adjustment can be performed by a back-propagation algorithm. Adjusting TADJ-1 the first trained function is in particular performed by a training computation unit TSYS.CU.

The steps of receiving TREC-1 the first medical image IMG1, receiving TREC-2 the first annotated data, determining TDET-1 a mask MASK1 of the airway wall depicted in the first medical image IMG1 and of adjusting TADJ-1 the first trained function can be repeated several times. In particular, in each repetition another first medical image IMG1 is received. Consequently, the first annotated data and the determined mask MASK1 also differ in between the repetitions because they are related to the first medical image IMG1. This repeated execution of the method can be denoted as training the first trained function.

In a first step of training the first trained function the first annotated data is automatically annotated data based on a first plurality of first medical images IMG1. This sequence of the training can be called pre-training. The first automatically annotated data is error prone.

Nevertheless, it can be used to pre-train the weights of the first trained function. In particular, the number of training datasets used in the pre-training is 2 times higher than the number of training datasets in the manual training (see second step of training), in particular 5 times higher, in particular 10 times higher, in particular 20 times higher. This allows to pre-train the first trained function based on this huge amount of first annotated data which improves the quality of the first trained function. As more training data, that means as more first medical images IMG1 with corresponding first annotated data are available for training as better are the output data of the first trained function.

In a second step of training the first trained function the first annotated data is first manually annotated data based on a second plurality of first medical images IMG1. The weights of the first trained function which has been pre-trained with the first automatically annotated data can like this be fine-tuned. In particular, the first manually annotated data is more precise and less error prone than the first automatically annotated data. Nevertheless, according to the above mentioned relations of first automatically annotated data and manually annotated data, there is in particular 2 times less (in particular 5 times less, in particular 10 times less, in particular 20 times less) first manually annotated data available than first automatically annotated data because the manual annotation of the second plurality the first medical images IMG1 is time-consuming. Nevertheless, the weights of an appropriately pre-trained function can be adjusted by training with just a few first manually annotated data.

The last step of the embodiment shown is providing TPROV-1 the first trained function.

In particular, this embodiment of the method for providing the first trained function can be analogue transferred to a method for providing the second trained function. The only difference are the input data, the annotated data and the output data. For the first trained function the input data comprises at least one first medical image, the annotated data comprises at least one mask which is either automatically or manually annotated and the output data comprises at least one mask. For the second trained function the input data comprises at least one second medical image, the annotated data comprises at least one airway probability map which is either automatically or manually annotated and the output data comprises at least one airway probability map.

Figure 8:
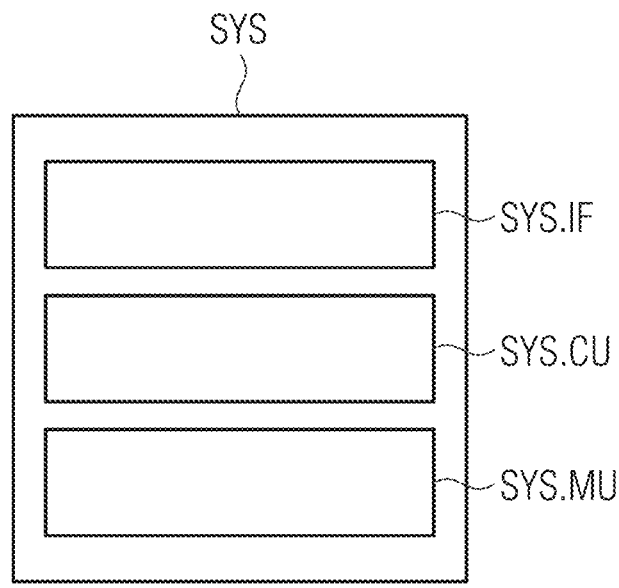
Figure 9:
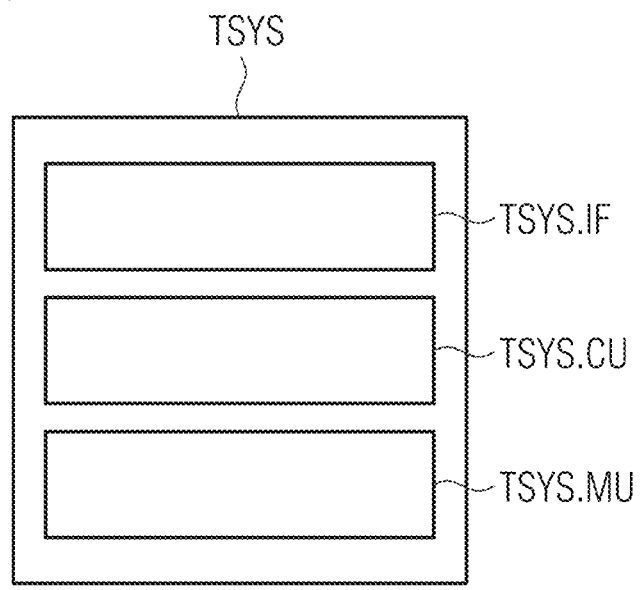

FIG. 8 displays a providing system SYS, FIG. 9 shows a training system TSYS. The displayed providing system SYS is configured to execute a method according to the invention for providing at least one quantitative airway information INFO1 or for providing an airway centerline tree CTREE1. The training system TSYS shown is designed to carry out a method according to the invention for providing a trained function. The following description hold true for the first and the second providing system, and the first and the second training system, according to the invention. The providing system SYS comprises an interface SYS.IF, a computation unit SYS.CU, and a memory unit SYS.MU. The training system TSYS comprises a training interface TSYS.IF, a training computational unit TSYS.CU, and a training memory unit TSYS.MU The providing system SYS and/or the training system TSYS can in particular be a computer, a microcontroller or an integrated circuit. Alternatively, the providing system SYS and/or the training system TSYS can be a real or a virtual network of computers (a technical term for a real network is "cluster", a technical term for a virtual network is "cloud"). The providing system SYS and/or the training system TSYS can also be designed as virtual system that is executed on a computer, a real network of computers or a virtual network of computers (a technical term is "virtualization").

An interface SYS.IF and/or a training interface TSYS.IF can be a hardware or software interface (for example PCI bus, USB or Firewire). A computation unit SYS.CU and/or a training computation unit TSYS.CU can have hardware elements or software elements, for example a microprocessor or a so-called FPGA (acronym for "field programmable gate way"). A memory unit SYS.MU and/or a training memory unit TSYS.MU can be implemented as a non-permanent working memory (random access memory, RAM for short) or as a permanent mass storage device (hard disk, USB stick, SD card, solid state disk).

The interface SYS.IF and/or the training interface TSYS.IF can in particular comprise a plurality of sub-interfaces which carry out different steps of the respective method. In other words, the interface SYS.IF and/or the training interface TSYS.IF can also be understood as a plurality of interfaces SYS.IF and/or a plurality of training interfaces TSYS.IF. The computation unit SYS.CU and/or the training computation unit TSYS.CU can in particular comprise a plurality of sub-computing units which carry out different steps of the respective method. In other words, the computation unit SYS.CU and/or the training computation unit TSYS.CU can also be understood as a plurality of computation units SYS.CU and/or a plurality of training computation units TSYS.CU.

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing at least one quantitative airway information, comprising:

determining whether a proposed airway segment is curved;
in response to determining that the proposed airway segment is curved, subdividing the proposed airway segment into one or more segments and adding the one or more segments to a plurality of airway segments of an airway centerline tree;
in response to the proposed airway segment not being curved, adding the proposed airway segment to the plurality of airway segments;
determining first medical image data of an airway segment, the airway segment being selected from the plurality of airway segments;
applying a first trained function to the first medical image data, to generate output data, the output data including a mask of a wall of the airway segment;
determining the at least one quantitative airway information of the airway segment based on the output data; and
providing the at least one quantitative airway information, wherein
the airway segment is a portion of the airway centerline tree that is not curved,
the first medical image data is a slice that is extracted from second medical image data, the slice being orthogonal to the airway segment such that the slice includes a cross-section of the airway segment, and
the first medical image data is determined based on the airway centerline tree and the second medical image data.

2. The method of claim 1, wherein the at least one quantitative airway information relates to thickness of the wall of the airway segment.

3. The method of claim 2, wherein the at least one quantitative airway information includes at least one of:
a wall thickness of the airway segment,
a lumen radius of the airway segment,
an outer wall radius of the airway segment, and
a wall percentage of the airway segment.

4. The method of claim 3, further comprising:
determining a classification value of a COPD state based on the at least one quantitative airway information.

5. The method of claim 1, wherein the first medical image data is two-dimensional and the second medical image data is three-dimensional.

6. The method of claim 1, further comprising:
receiving the second medical image data;
applying a second trained function to the second medical image data, to generate an airway probability map; and
applying a skeletonization algorithm on the airway probability map to determine the airway centerline tree.

7. A non-transitory computer program product storing program elements, directly loadable into a memory unit of a first providing system, to induce a providing system to execute the method of claim 1 when the program elements are executed by the providing system.

8. A non-transitory computer-readable storage medium storing program elements, readable and executable by a providing system, to execute the method of claim 1 when the program elements are executed by the providing system.

9. The method of claim 2, further comprising:
determining a classification value of a COPD state based on the at least one quantitative airway information.

10. The method of claim 1, wherein the mask of the wall of the airway segment is a binary mask.

11. The method of claim 10, wherein the mask of the wall of the airway segment is a same size as a first medical image and each pixel of the mask of the wall of the airway segment indicates whether a corresponding pixel of the first medical image represents the wall of the airway segment.

12. The method of claim 1, wherein the mask of the wall of the airway segment includes information about a density of the wall of the airway segment.

13. The method of claim 12, wherein the information about the density of the wall is encoded in intensity values of pixels within an image of the mask of the wall.

14. The method of claim 1, wherein the airway centerline tree includes a plurality of points, the airway segment being a section of the airway centerline tree between a first point of the plurality of points and a second point of the plurality of points.

15. The method of claim 1, wherein the cross-section of the airway segment is circular.

16. A computer implemented method for providing a first trained function, comprising:
receiving first medical image data of a first airway segment;
receiving first annotated data, the first annotated data being based on the first medical image data, and the first annotated data being a mask of a wall of the first airway segment;
training the first trained function based on the first medical image data and the first annotated data; and
providing the first trained function.

17. The method of claim 16, further comprising:
receiving first pre-training medical image data of a second airway segment;
determining a pre-training mask of a wall of the second airway segment based on a first deterministic algorithm; and
pre-training the first trained function based on the first pre-training medical image data and the pre-training mask.

18. The method of claim 17, wherein the first deterministic algorithm is based on a Full-Width-Half-Maximum Segmentation.

19. A non-transitory computer-readable storage medium, storing the first trained function provided by the method of claim 16.

20. A first providing system for providing at least one quantitative airway information, comprising:
an interface; and
a computation unit, wherein
the computation unit is configured to determine whether a proposed airway segment is curved,
in response to determining that the proposed airway segment is curved, the computation unit is configured to subdivide the proposed airway segment into one or more segments and add the one or more segments to a plurality of airway segments of an airway centerline tree,
in response to the proposed airway segment not being curved, the computation unit is configured to add the proposed airway segment to the plurality of airway segments,
at least one of the interface and the computation unit is configured to at least one of receive or determine first medical image data of an airway segment, the airway segment being selected from the plurality of airway segments,
the computation unit is configured to apply a first trained function to the first medical image data, to generate output data, the output data including a mask of a wall of the airway segment, the computation unit is configured to determine the at least one quantitative airway information of the airway segment based on the output data, the interface is configured to provide the at least one quantitative airway information, the first medical image data is a slice that is extracted from second medical image data, the slice being orthogonal to a part of the airway centerline tree corresponding to the airway segment such that the slice includes a cross-section of the airway segment, and the first medical image data is determined based on the airway centerline tree and the second medical image data.

* * * * *